(12) United States Patent
Moses et al.

(10) Patent No.: US 8,911,765 B2
(45) Date of Patent: *Dec. 16, 2014

(54) BIODEGRADABLE, POLYMER COVERINGS FOR BREAST IMPLANTS

(75) Inventors: Arikha Moses, New York, NY (US); Satish Pulapura, Bridgewater, NJ (US); Qing Ge, Plainsboro, NJ (US); Sarita Nethula, Monmouth Junction, NJ (US); Irene Shatova, Jamesburg, NJ (US); Archana Rajaram, Monmouth Junction, NJ (US)

(73) Assignee: Tyrx, Inc., Monmouth Junction, NJ (US)

( * ) Notice: Subject to any disclaimer, the term of this patent is extended or adjusted under 35 U.S.C. 154(b) by 136 days.

This patent is subject to a terminal disclaimer.

(21) Appl. No.: 12/058,060

(22) Filed: Mar. 28, 2008

(65) Prior Publication Data

US 2008/0241212 A1  Oct. 2, 2008

Related U.S. Application Data

(60) Provisional application No. 60/983,108, filed on Oct. 26, 2007, provisional application No. 60/908,960, filed on Mar. 29, 2007.

(51) Int. Cl.
| | | |
|---|---|---|
| *A61F 2/12* | (2006.01) | |
| *A61K 31/496* | (2006.01) | |
| *A61K 31/65* | (2006.01) | |
| *A61K 31/7036* | (2006.01) | |
| *A61K 38/00* | (2006.01) | |
| *A61K 31/48* | (2006.01) | |
| *A61K 31/545* | (2006.01) | |
| *A61K 31/47* | (2006.01) | |
| *A61K 31/41* | (2006.01) | |
| *A61K 31/404* | (2006.01) | |
| *A61K 31/381* | (2006.01) | |
| *A61K 31/167* | (2006.01) | |
| *A61K 31/445* | (2006.01) | |
| *A61K 38/13* | (2006.01) | |
| *A61K 31/7048* | (2006.01) | |
| *B29C 41/14* | (2006.01) | |

(52) U.S. Cl.
CPC .................. *A61F 2/12* (2013.01); *A61K 31/545* (2013.01); *B29C 41/14* (2013.01); *A61K 31/41* (2013.01); *A61K 31/496* (2013.01); *A61K 31/381* (2013.01); *A61K 31/167* (2013.01); *A61K 31/65* (2013.01); *A61K 31/47* (2013.01); *A61K 38/13* (2013.01); *A61K 31/7048* (2013.01); *A61K 31/404* (2013.01); *A61K 31/7036* (2013.01); *A61K 31/445* (2013.01)
USPC .......... 424/426; 623/8; 514/254.11; 514/152; 514/40; 514/8; 514/27; 514/200; 514/311; 514/382; 514/415; 514/443; 514/626; 514/330

(58) Field of Classification Search
None
See application file for complete search history.

(56) References Cited

U.S. PATENT DOCUMENTS

| | | | |
|---|---|---|---|
| 4,298,997 A | 11/1981 | Rybka | |
| 4,642,104 A | 2/1987 | Sakamoto et al. | |
| 4,648,880 A | 3/1987 | Brauman | |
| 4,713,073 A | 12/1987 | Reinmuller | |
| 4,846,844 A | 7/1989 | De Leon et al. | |
| 4,889,744 A | 12/1989 | Quaid | |
| 5,099,060 A | 3/1992 | Kohn et al. | |
| 5,216,115 A | 6/1993 | Kohn et al. | |
| 5,217,493 A | 6/1993 | Raad et al. | |
| 5,250,020 A * | 10/1993 | Bley ............................... 600/40 |
| 5,317,077 A | 5/1994 | Kohn et al. | |
| 5,376,117 A | 12/1994 | Pinchuk et al. | |
| RE35,391 E | 12/1996 | Brauman | |
| 5,607,477 A | 3/1997 | Schindler et al. | |
| 5,624,704 A | 4/1997 | Darouiche et al. | |
| 5,630,844 A | 5/1997 | Dogan | |
| 5,653,755 A | 8/1997 | Ledergerber | |
| 5,658,995 A | 8/1997 | Kohn et al. | |
| 5,902,283 A | 5/1999 | Darouiche et al. | |
| 6,013,853 A | 1/2000 | Athanasiou | |
| 6,048,521 A | 4/2000 | Kohn et al. | |
| 6,103,255 A | 8/2000 | Levene et al. | |
| 6,120,491 A | 9/2000 | Kohn et al. | |

(Continued)

FOREIGN PATENT DOCUMENTS

| | | |
|---|---|---|
| JP | 2004130118 A | 4/2004 |
| JP | 2005137398 A | 6/2005 |
| JP | 2005537909 A | 12/2005 |
| WO | WO 99/24107 | 5/1999 |
| WO | WO 07/056134 | 5/2007 |
| WO | PCT/US08/62582 | 5/2008 |
| WO | WO 2008/075398 | * 6/2008 |

OTHER PUBLICATIONS

Kohn. "Implants: The Biodegradable Future" 2006. http://www.medicaldevice-network.com/features/feature168/.*

(Continued)

*Primary Examiner* — Robert A Wax
*Assistant Examiner* — Danah Al-Awadi
(74) *Attorney, Agent, or Firm* — Sorell, Lenna & Schmidt, LLP

(57) ABSTRACT

A biodegradable, flexible covering for a breast implant is provided which comprises one or more biodegradable polymer layers dimensioned and shaped to cover at least a portion of the breast implant. The implant can be inserted into an opening of the covering immediately prior to surgery, but alternate configurations and times of insertion are contemplated as well as open or sheet type devices. The coverings can optionally contain one or more drugs for delivery at the surgical site, particularly for treating or preventing infection, pain, inflammation, capsular contracture, scarring or other complications associated with breast augmentation or breast reconstruction.

29 Claims, 7 Drawing Sheets

(56) References Cited

U.S. PATENT DOCUMENTS

| | | | |
|---|---|---|---|
| 6,214,045 | B1 | 4/2001 | Corbitt, Jr. et al. |
| RE37,160 | E | 5/2001 | Kohn et al. |
| 6,267,772 | B1 | 7/2001 | Mulhauser et al. |
| 6,298,998 | B1 | 10/2001 | Mani |
| 6,319,492 | B1 | 11/2001 | Kohn et al. |
| 6,337,198 | B1 | 1/2002 | Levene et al. |
| 6,382,526 | B1 | 5/2002 | Reneker et al. |
| RE37,795 | E | 7/2002 | Kohn et al. |
| 6,475,477 | B1 | 11/2002 | Kohn et al. |
| 6,544,287 | B1 | 4/2003 | Johnson et al. |
| 6,548,569 | B1 | 4/2003 | Williams et al. |
| 6,558,686 | B1 | 5/2003 | Darouiche |
| 6,602,497 | B1 | 8/2003 | Kohn et al. |
| 6,656,488 | B2 | 12/2003 | Yi et al. |
| 6,852,308 | B2 | 2/2005 | Kohn et al. |
| 6,887,270 | B2 | 5/2005 | Miller |
| 6,913,626 | B2 | 7/2005 | McGhan |
| 6,916,483 | B2 | 7/2005 | Ralph |
| 6,951,869 | B2 | 10/2005 | Schlesinger |
| 6,969,400 | B2 | 11/2005 | Rhee |
| 6,974,862 | B2 | 12/2005 | Ringeisen |
| 6,991,802 | B1 | 1/2006 | Ahola |
| 7,005,454 | B2 | 2/2006 | Brocchini |
| 7,056,493 | B2 | 6/2006 | Kohn et al. |
| 7,250,154 | B2 | 7/2007 | Kohn et al. |
| 7,271,234 | B2 | 9/2007 | Kohn et al. |
| 7,326,425 | B2 | 2/2008 | Kohn et al. |
| 8,315,700 | B2 * | 11/2012 | Citron et al. ............ 607/5 |
| 2002/0072694 | A1 | 6/2002 | Snitkin et al. |
| 2003/0030940 | A1 | 2/2003 | Matono |
| 2003/0138488 | A1 | 7/2003 | Kohn et al. |
| 2003/0162828 | A1 | 8/2003 | Schlesinger |
| 2003/0175410 | A1 | 9/2003 | Campbell et al. |
| 2004/0010276 | A1 | 1/2004 | Jacobs et al. |
| 2004/0010854 | A1 | 1/2004 | Oakhill et al. |
| 2004/0043052 | A1 | 3/2004 | Hunter |
| 2004/0197374 | A1 * | 10/2004 | Rezania et al. ............ 424/426 |
| 2004/0220249 | A1 | 11/2004 | Puder et al. |
| 2004/0245671 | A1 | 12/2004 | Smit |
| 2004/0254334 | A1 | 12/2004 | James et al. |
| 2005/0079365 | A1 | 4/2005 | Widenhouse et al. |
| 2005/0101692 | A1 | 5/2005 | Sohier et al. |
| 2005/0147690 | A1 | 7/2005 | Masters et al. |
| 2005/0163821 | A1 | 7/2005 | Sung et al. |
| 2005/0181007 | A1 | 8/2005 | Hunter et al. |
| 2005/0208095 | A1 | 9/2005 | Hunter et al. |
| 2005/0209664 | A1 | 9/2005 | Hunter et al. |
| 2005/0228471 | A1 | 10/2005 | Williams et al. |
| 2005/0244459 | A1 | 11/2005 | DeWitt et al. |
| 2006/0009806 | A1 | 1/2006 | Heruth et al. |
| 2006/0025852 | A1 | 2/2006 | Armstrong et al. |
| 2006/0035854 | A1 | 2/2006 | Goldstein et al. |
| 2006/0095134 | A1 | 5/2006 | Trieu et al. |
| 2006/0115449 | A1 | 6/2006 | Pacetti |
| 2006/0154063 | A1 * | 7/2006 | Fujihara et al. ............ 428/373 |
| 2006/0204440 | A1 | 9/2006 | Kohn et al. |
| 2007/0196421 | A1 * | 8/2007 | Hunter et al. ............ 424/423 |
| 2007/0198040 | A1 | 8/2007 | Buevich et al. |
| 2007/0299155 | A1 * | 12/2007 | Carpenter et al. ............ 523/105 |
| 2008/0091276 | A1 * | 4/2008 | Deusch et al. ............ 623/23.72 |
| 2008/0107709 | A1 | 5/2008 | Kohn et al. |
| 2008/0128315 | A1 * | 6/2008 | Buevich et al. ............ 206/572 |
| 2008/0132922 | A1 | 6/2008 | Buevich et al. |
| 2009/0018559 | A1 | 1/2009 | Buevich et al. |

OTHER PUBLICATIONS

Kohn. "implants: The Biodegradable Future" 2006.*
Adams et al., 2006, "A Rabbit Model for Capsular Contracture: Development and Clinical Implications," Plastic and Reconstructive Surgery 117(4):1214-1219.
Adams et al., 2006, "Enhancing Patient Outcomes in Aesthetic and Reconstructive Breast Surgery Using Triple Antibiotic Breast Irrigation: Six-Year Prospective Clinical Study," Plastic and Recon. Surg. 117(1):30-36.
Adams et al., 2001, "Optimizing Breast-Pocket Irrigation: The Post-Betadine Era," Plast Reconstr Surg. 107(6):1596-1601.
Ajmal et al., 2003, "The effectiveness of sodium 2-mercaptoethane sulfonate (mesna) in reducing capsular formation around implants in a rabbit model," Plast. Reconstr. Surg. 112(5):1455-1461.
Darouiche et al., 2002, "In vivo Efficacy of Antimicrobe-Impregnated Saline-Filled Silicone Implants," Plast Reconstr Surg. 109(4):1352-1357.
Erkin et al., 2007, "Influence of Rifampin on Capsule Formulation Around Silicone Implants in a Rat Model.," Aesth. Plast. Surg. 31:358-364.
Hedrick et al., 2006, "Implant-Associated Infections: An Overview," J. Long-Term Effects Medical Implants 16(1)83-99.
Pittet et al., 2005, "Infection in Breast Implants," Lancet Infect. Dis. 5:94-106.
Poeppl et al., 2007, "Does the Surface Structure of Implants Have an Impact on the Formation of a Capsular Contracture?" Aesth. Plast. Surg. 31:133-139.
Rohrich et al., 1999, "Preventing Capsular Contracture in Breast Augmentation: In Search of the Holy Grail," Plast. Reconstr. Surg. 103(6)1759-1760.
Subbiah et al., 2005. "Electrospinning of nanofibers," J. Appl. Poly. Sci. 96(2):557-569.
PCT International Search Report (ISR) for corresponding PCT international patent application PCT/US08/58652, mailed Sep. 12, 2008, 4 pp.
Written opinion for corresponding PCT international patent application PCT/US08/58652, mailed Sep. 12, 2008, 4 pp.
Yourassowsky, E. et al., "Combination of Minocycline and Rifampicin against Methicillin- and Gentamicin-Resistant *Staphylococcus aureus*," J. Clin. Pathol., 1981, pp. 559-563, vol. 34.
Clumeck, N. et al., "Treatment of Severe Staphylococcal Infections with a Rifampicin-Minocycline Association," J. Antimicrob. Chemother., 1984, pp. 17-22, vol. 13(SuppC).
Zinner, S. H. et al., "Antistaphylococcal Activity of Rifampin with Other Antibiotics," J. Infect. Dis., Oct. 1981, pp. 365-371, vol. 144(4).
van't Riet, M. et al., "Prevention of Adhesion Formation to Polypropylene Mesh by Collagen Coating," Surg. Endosc., 2004, pp. 681-685, vol. 18.
Office Action for U.S. Appl. No. 11/672,929, mailed Feb. 3, 2010, 11 pages.
Office Action for U.S. Patent Application No. 11/936,049, mailed Apr. 14, 2010, 18 pages.
International Search Report and Written Opinion for International Application No. PCT/US2007/083841, mailed on Oct. 31, 2008, 8 pages.
International Preliminary Report on Patentability for International Application No. PCT/US2007/083841, issued on May 12, 2009, 6 pages.
International Search Report and Written Opinion for International Application No. PCT/US2007/083843, mailed on Sep. 11, 2008, 7 pages.
International Preliminary Report on Patentability for International Application No. PCT/US2007/083843, issued on May 12, 2009, 7 pages.
Canter et al., Aest Plast Surg, 31; 674-679 (2007).
Costerton et al., The Journal of Clinical Investigation, 112(10); 1466-1477 (2003).
Prantl et al., Plastic and Reconstructive Surgery, Jul. 2007, 275-284.
Australian Examination Report for Application No. 2008232682 dated Jun. 20, 2012.
Japanese Office Action for Application No. 2010-501255 dated Dec. 18, 2012.
Canadian Office Action for Application No. 2,682,190 dated Nov. 15, 2013.
Extended European Seach Report for Allication No. EP 08799713 dated Aug. 1, 2013.
Handel et al: "Long-term safety and efficacy of polyurethane foam-covered breast implants". Aesthetic Surgery Journal, Mosby-Year Book, St. Louis, MO, US, vol. 26, No. 3, May 1, 2006, pp. 265-274.

* cited by examiner p(DTE:15% DT-co-succinate)

R = 85%  —O—CH$_2$ CH$_3$ ,15% OH p(DTE-co-(50:50 PEG600 acid:adipate))

R$_1$ = 50%  —CH$_2$CH$_2$CH$_2$-CH$_2$—  , 50%  —CH$_2$O(CH$_2$CH$_2$O)$_n$CH$_2$— p(DTE-co-(50:50 PEG400 bis-succinate:adipate))

R$_1$ = 50%  —CH$_2$CH$_2$CH$_2$-CH$_2$—  , 50%  —CH$_2$CH$_2$C(=O)—O(CH$_2$CH$_2$O)$_n$C(=O)—CH$_2$CH$_2$—

BIODEGRADABLE, POLYMER COVERINGS FOR BREAST IMPLANTS

This application claims priority under 35 U.S.C. §119(e)(5) to U.S. Provisional Patent Application No. 60/983,108, filed Oct. 26, 2007 and of U.S. Provisional Patent Application No. 60/908,960, filed Mar. 29, 2007, which are incorporated herein by reference.

FIELD OF THE INVENTION

A biodegradable, flexible covering for a breast implant is provided which comprises one or more biodegradable polymer layers dimensioned and shaped to cover at least a portion of the breast implant. The implant can be inserted into an opening of the covering immediately prior to surgery, but alternate configurations and times of insertion are contemplated as well as open or sheet type devices. The coverings can optionally contain one or more drugs for delivery at the surgical site, particularly for treating or preventing infection, pain, inflammation, capsular contracture, scarring or other complications associated with breast augmentation or breast reconstruction.

BACKGROUND OF THE INVENTION

Localized complications are a common occurrence in breast augmentation and breast reconstruction surgery. Among the more serious of these surgical complications are infection, capsular contracture, hematoma and pain. Women who have undergone radiation therapy as part of their breast cancer treatment appear to sustain higher rates of post-surgical infection and capsular contracture.

Infection can occur anytime from several days to several years after implantation; however, it occurs more frequently in the immediate post-operative period. Acute infection is diagnosed when the patient exhibits pain, fever, and tenderness around the implant between several days and six weeks from the time of surgery. According to one report, the incidence of infection ranges from 1-24% (Nahabedian et al. (2003) Plast. Reconstr. Surg. 112:467-76) with *Staphylococcus aureus, Propionii acne* and *Staphylococcus epidermis* among the cultured bacteria from colonized implants (Pittet et al (2005) Lancet Infect. Dis. 5:94-106).

Another issue arising with the use of breast implants is the formation of excess scar tissue around an implant. Such tissue can harden and lead to tightening around or squeezing of the implant, a phenomenon known as capsular contracture. While scar tissue and capsule formation is a normal process, when capsular contracture occurs the breast can become misshapen, painful, hard and attain an unnatural appearance and feel. Additionally, capsular contracture appears to be more common following infection, hematoma and seroma. Textured implant surfaces and submuscular placement of the implant may decrease the rate of capsular contracture (FDA Breast Implant Consumer Handbook, 2004, p. 28).

Implant infection is most commonly attributed to contamination of the sterile field during surgery or to contamination arising from lymph node or mammary duct dissection during surgery. Bacteria can migrate deep within the breast tissue via the mammary ducts. Incision through the ducts during subglandular placement thus opens a temporary but direct external route for contamination of the implant after placement. Bacteria colonized from the mammary ducts and nipples is similar to exogenous flora found on the skin, namely coagulase negative *Staphylococcus, P. acne*, and *Bacillus subtillus* (Pittet, supra).

Subclinical infection is perceived to be the a contributor to capsular contracture. Subclinical infection is defined as bacterial colonization of a surface with or without biofilm formation. It does not produce the signs and symptoms traditionally associated with frank infection (such as pain, tenderness, fever, and pus) and manifests itself as a chronic inflammatory response. This inflammatory response can produce constant tissue remodeling that leads to fibrous tissue buildup and eventual implant distortion and capsule rigidity.

Most surgeons engage in prophylactic efforts to reduce the incidence of infection associated with breast implants. For example, in addition to meticulous attention to sterility, many surgeons irrigate the implant pocket with betadine, gentamycin, cefazolin, povidone-iodine or another antibiotic solution. Post-operative counseling measures include instructing the patient to neither touch the incision sites nor to immerse them in hot water for at least two weeks (or until healing is complete). Prophylactic oral antibiotics can also given to patients prior to surgery to prevent post-implant colonization. Additionally, implant placement below the muscle avoids (or at least minimizes) surgical contact with the mammary ducts.

Adams and colleagues devised a method for reducing capsular contracture caused by bacterial implant colonization. They optimized the antibacterial irrigation solution and employed sterile technique prior to and during surgery. Adams' "triple antibiotic solution" originally contained a mixture of bacitracin, gentamycin, and cefazolin and was shown to be active against bacteria most commonly known to colonize breast implants. Adams subsequently published results of a six-year clinical study showing that patients who received surgeries incorporating these techniques have a 1% capsular contracture rate as opposed to national rates, which approached 15-20% in that same time period (Adams et al. (2006) Plast. Reconstr. Surg. 117:30-36).

To increase the length of time during which an antibiotic or antimicrobial agent resides within the vicinity of the breast implant, Darouiche and colleagues soaked silicone breast implants with a combination of rifampin and minocycline and implanted them in a rabbit model. While the antibiotic-soaked implants prevented bacterial colonization relative to unsoaked control implants, the soaking process caused the antibiotics to leach into the silicone gel as evidenced by implant swelling. In another instance, surgeons injected povidone-iodine solution directly into the breast implant but this entails a risk because the silicone shell can weaken and leak. In fact, the FDA has stated that povidone-iodine is contraindicated for use with breast implants as a result of reported ruptures with its use.

Some of the efforts to reduce capsular contracture involve post-operative measures, including counseling the patient to massage the implant (after the initial healing period is complete) and taking vitamin E. Once capsular contracture has occurred, anecdotal evidence indicates that orally-administered leukotriene receptor antagonists can reduce the amount of capsular contracture (U.S. Pat. No. 6,951,869 to Schlesinger).

Texturing the outside silicone surface has been employed as a technique to prevent capsular contracture. The textured surface is believed to be more biocompatible and to promote tissue ingrowth. However, these implants have not significantly penetrated the market because, in use, the implants may become firmly placed under the skin, which often leads to a visible dimpling effect when the recipient moves. Textured implants also tend to have thicker shells than smooth implants and higher rupture rates.

Quaid describes a method in which a biocompatible, non-bioabsorbable uncured silicone elastomer is applied to the outer surface of a silicone implant to create an outer layer (U.S. Pat. No. 4,889,744). Solute particles, usually salt, are embedded in the tacky layer which is then partially cured, exposed to an appropriate solvent to remove the solute particles, and then fully cured. The plurality of voids remaining in the layer following removal of solute from the fully-cured, outer layer leaves an open celled structure. The resulting medical implant has both a textured outer surface and unitary construction. McGhan describes hybrid implants made with a biocompatible, bioabsorbable material adhered to the typically silicone shell of the implant (U.S. Pat. No. 6,913,626. In one embodiment, McGhan's implants have discrete bioabsorbable particles partially embedded in the outer shell.

Brauman describes breast implants with a layer laminated or bonded (e.g., glued) to the implant shell (U.S. Pat. No. 4,648,880 and RE35,391). The layer has a rough textured surface and is made from non-biodegradable material such as Dacron® (poly(ethylene glycol terephthalate)), Teflon® or silicone. Brauman's implants may optionally contain a barrier layer bonded between the shell and the outer layer. Such implants are susceptible to delaminating within the body.

The partial or total adhesion of the implant to the capsule due to such tissue ingrowth may be undesirable in the event it becomes necessary to remove or replace the implant. Further, partial or asymmetric adhesion between the capsule and the outer surface of the implant may give rise to undesirable cosmetic effects. Notwithstanding the foregoing disadvantages, textured implants having a biocompatible, non-bioabsorbable outer tissue-contacting surface are generally considered to reduce the incidence of capsular contracture in patients. Nevertheless, there remains a need for an implantable fluid-filled prosthesis that resists capsular contracture following implantation and that resists adherence of the implant to the capsule.

The biodegradable coverings of the present invention overcome these drawbacks while reducing or preventing capsular contracture as well as treating or preventing infection, pain, inflammation, scarring or other complications associated with breast augmentation or breast reconstruction.

SUMMARY OF THE INVENTION

The present invention is directed to biodegradable elastomeric coverings for breast implants. In certain embodiments, these coverings comprise one or more biodegradable polymer layers dimensioned and shaped to cover at least a portion of the breast implant. Such coverings have an outer surface to engage tissue, an inner surface directed toward the breast implant and a peripheral edge defining a flexible opening for receiving the implant. In other embodiments, the coverings are sheets, films, or mats of one or more biodegradable polymer layers that can be wrapped or cut into the dimension and shape of a breast implant and thereby used to cover at least a portion of the breast implant, for example, in an annular fashion around the periphery of the breast implant shell. Hence, a covering of the invention can inhibit or reduce formation of scar tissue in and around the implant and/or inhibit or reduce capsular contracture in and around the implant in a patient. When drugs are present in the polymer matrix that forms the cover, such drugs can elute into the surrounding tissue to provide therapeutic efficacy, such as pain relief for analgesics and inhibition or prevention of bacterial infection or colonization for antimicrobial agents (antibiotics).

For example, the coverings with selection of appropriate antibiotics, can provide protection against colonization by bacteria most commonly known to colonize implants for at least one week, but preferably between two and four weeks. The covering provides a sterile barrier around the implant that can both kill any contaminating bacteria from the surgical insertion itself as well as elute antimicrobial agents after surgery to prevent bacterial migration to the implant during the healing process.

The covering of the invention can comprise multiple layers, typically from one to five layers. In one embodiment, the coverings can include an inner barrier layer facing the breast implant shell, one or more central polymeric layers that can optionally contain one or more drugs, and an outer polymeric layer that can be smooth or textured and optionally contain one or more drugs. The polymeric central and outer layers can be made of the same or different biodegradable polymers. When a barrier layer is used, that layer forms the inner surface that faces the implant shell that is drug impermeable during the drug release phase post-implantation. The barrier layer is also biodegradable with degradation and resorption occurring after drug release (or on a time scale that maintains impermeability of the barrier sufficient to prevent any significant migration of the drug into the breast implant.

Any of the coverings of the invention can substantially or partially encase the breast implant. Likewise the coverings can wrap the outer annular portion of the breast implant, act as a cup or cap in which the breast implant is placed, or be a sheet inserted between the implant and the tissue of the insertion pocket.

The polymeric layers of the covering are made with a biodegradable polymer, and preferably from tyrosine-derived polyarylates.

Another aspect of the invention is directed to a kit comprising a breast implant and the biodegradable covering of the inventions.

In another aspect, the present invention provides a breast implant assembly comprising, in sterile form, a biodegradable covering of the invention containing, wrapped around or otherwise engaging a breast implant so that handling or manipulation of the assembly is minimized during surgery.

Yet a further aspect of the invention is directed to a method for reducing post-surgical complications, such as capsular contracture or infection, from breast augmentation, breast reconstruction or breast restoration in a subject which comprises surgically implanting a breast implant assembly of the invention into the subject.

DETAILED DESCRIPTION OF THE INVENTION

Figure 1:
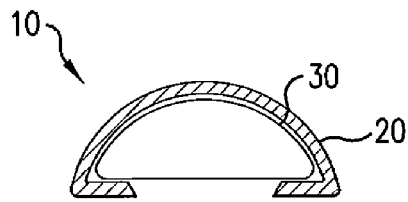
FIG. 1 shows a projection view of a breast implant assembly 10 with the covering 20 encasing the breast implant 30.

The present invention is directed to biodegradable elastomeric coverings for breast implants. The coverings have form-fitting shapes for the implant and are generally placed over an implant in the operating room prior to its insertion during surgery. The coverings can also be preassembled with the breast implant and supplied in that form to the surgical team.

In some embodiments, while the biodegradable covering has substantially the same shape and size as the implant itself (e.g., round, teardrop, contoured, anatomical and the like), it does not completely cover the implant. In some embodiments, the coverings are shaped like shower caps. In other embodiments, while also shaped like a shower cap or formed to fit the implant, the covering is slightly smaller than the breast implant and can be stretched and shrunk, typically by heating and cooling, to fit snugly on the implant. In some embodiments, the partial coverings fit the back and a minimal amount of the sides of the implant and, while retaining a size appropriate to the particular implant, approximate a shaped sheet or a shallow cup. The biodegradable coverings and sheets of the invention are useful to reduce capsular contracture and to deliver drugs into the surrounding tissue, to facilitate healing or to prevent infection, pain, and/or other morbidities associated with breast implants.

General Aspects of the Coverings

In accordance with the invention, the biodegradable coverings of the invention comprise one or more biodegradable (elastomeric) polymer layers dimensioned and shaped to cover at least a portion of the breast implant. The coverings have an outer surface (that faces or engages tissue), an inner surface (that faces or engages the implant shell) and a peripheral edge defining a flexible opening for receiving the implant. In some embodiments, the flexible opening opens to the back (posterior side) of the implant. In other embodiments, the flexible opening opens to the front (anterior side) of the implant. Such coverings, especially those with openings in the back, appear similar in shape to shower caps. The flexible openings can be stretched and reformed to fit around the implant much like the elastic band of a shower cap that stretches for wearing and then to shrinks back to fit snugly like a seal around the bathers' hair. It should be noted that the coverings of the invention do not form a seal on the breast implant. Another shape for the covering is a jelly fish-like shape (a rounded cap with extending tendrils) where the covering covers one side of the breast implant shell. Open-front or open-back coverings that do not fully cover the convex front surface of the breast implant shell can be considered "cap" like or "jelly-fish" like, with the latter having tendrils that may or may not lay across the front convex surface (or the back when open to the back).

Front opening covers (e.g., shaped like small, low-sided cups or caps) have an advantage for use with textured, anatomically-shaped implants (teardrop shaped) as it is believed, without being bound to a particular mechanism, that the interaction of the tissue with the textured surface is important to maintain the implant in proper orientation after implantation. Back opening covers have an advantage because they generally have more surface area and thus have higher drug loading capabilities. Breast implants are more easily inserted into coverings with larger openings, allowing for less manipulation and less risk of contamination during surgery. However, smaller, flexible openings mean that the cover can have a larger surface area for drug delivery and for contact with tissue. This latter ability may be important in preventing capsular contracture and for pocket integrity (allowing easier removal of the implant should the need arise).

FIG. 1 depicts a cross section view of an embodiment of the invention. In this embodiment, the breast implant assembly 10 has a covering 20 of generally uniform thickness over the breast implant shell 30. This covering has a flexible opening on the back or posterior side of the breast implant shell and is formed from a single biodegradable polymer layer.

Figure 2A:
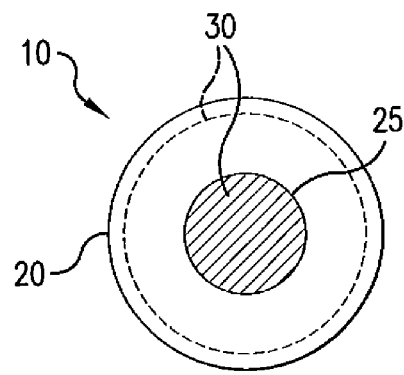
FIG. 2 provides a bottom view of a breast implant assembly 10 to illustrate a large round opening 25. A 3-D schematic of a breast implant assembly is also shown as part of FIG. 2.
Figure 2B:
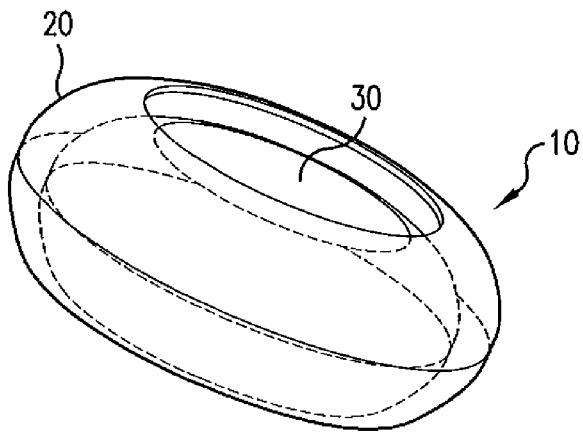
Figure 3:
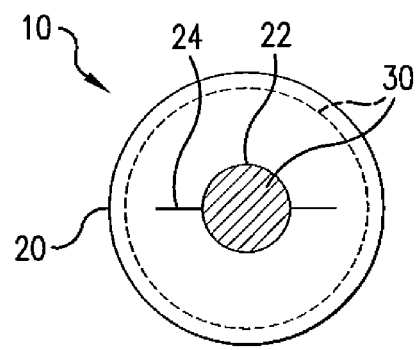
FIG. 3 provides a bottom view of a breast implant assembly 10 to illustrate a small round opening 22 with slits 24.
Figure 4:
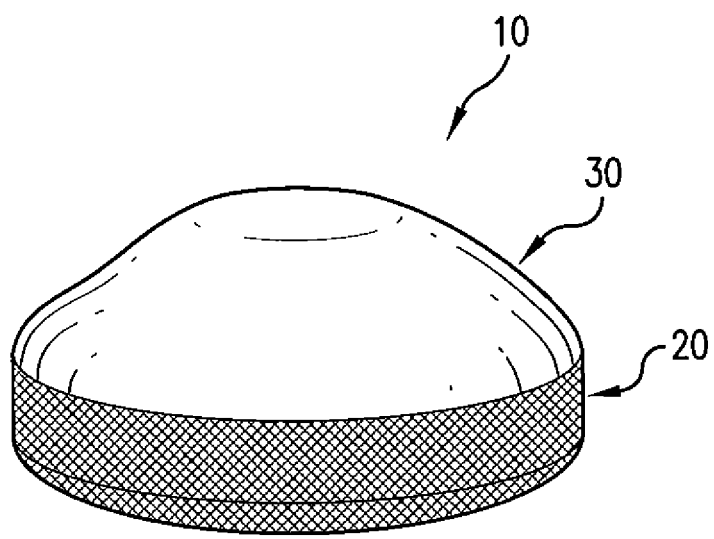
FIG. 4 depicts a side view of a breast implant assembly 10 with a covering 20 fit on the back of a textured implant 30.

The flexible openings are typically round and are sized to allow insertion of the implant into the covering and/or to achieve a variable amount of coverage of the back of the implant (for openings to the back) or front (for openings to the front). The flexible openings can have any shape that allows the covering to be manipulated to receive the implant and fit around the implant with a desired snugness. For example, FIG. 2 shows a covering 20 with a large opening 25 over the implant 30. FIG. 3 shows an alternative embodiment of the flexible opening in which the covering 20 has a small opening 22 and slits 24, thereby covering a greater area of the back of the implant. A single slit may suffice to provide a flexible opening provided that is compatible with the molding or manufacturing process for producing the covering. Multiple slits in any appropriate arrangement can also be used. Whether alone or in combination, the length of the slits, the size of the openings or the selected shape of the openings can be varied to provide an opening of a sufficient size and flexibility to allow the implant to be inserted in the covering as shown, e.g., in FIGS. 2 and 3. An example of a covering with an opening that leaves close to the entire front surface of a textured implant exposed is shown in FIG. 4. In another embodiment, the coverings can be designed to surround the circumference of the devise. For a round implant, the covering would be substantially cylindrical while curving to fit up onto the sides while leaving an opening to both the front and back of the implant. Those of skill in the art can readily determine appropriate shapes, sizes and configurations for the flexible openings for a given size breast implant.

Figure 5:
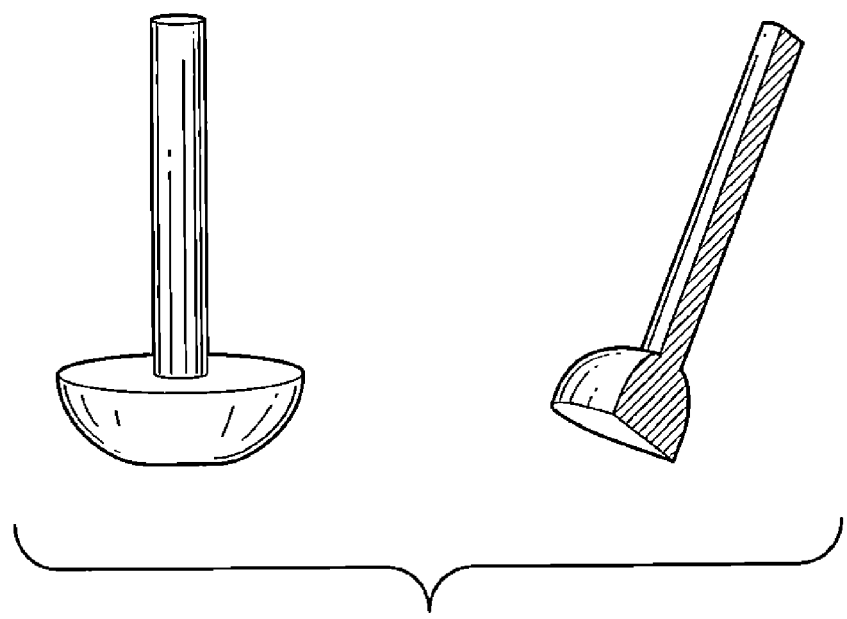
FIG. 5 depicts an exemplary mold that produces a shower cap-shaped covering (left panel) and a cut away view of an exemplary mold that produces a open-front covering (right panel). The edges of the mold, while depicted here as sharp, are preferably rounded.

Breast implants are commercially available and come in several shapes and a wide variety of sizes. Most breast implants currently in use consist of a strong silicone elastomer shell filled with a saline solution although implants filled with silicone gel are also in use. Breast implant shapes can be round, teardrop, contoured or anatomical shaped or the like. The terms teardrop, contoured or anatomical are generally interchangeable for describing implants having a shape more like the natural anatomical shape of a breast. Breast implants sizes are specified by device volume (usually in cc), diameter and projection (or profile). Commercially available implants range from 120 cc to 850 cc but larger sizes can be custom made. In accordance with the invention, a biodegradable covering can be made that fits any size implant, for example, by using a mold that matches the size and shape of the implant. Examples of molds are shown in FIG. 5.

The coverings of the invention can be made to fit any size breast implant, and can be made sufficiently flexible to accommodate a range of varying volume breast implants. Typically the coverings are designed for a particular range of volumes, with variances of about 25 to 75 cc being typical. In other words, a covering designed for a 300 cc implant can accommodate a 275 or 350 cc implant.

Methods of preparing the polymer layers for the dimensioned and shaped coverings of the invention include dip molding, spray coating and other methods which are conventional or known in the art. Materials for the molds are conventional such as plastics, like polypropylene, nylon, Teflon, and delrin peek, metals like stainless steel and titanium, as well as glass and, ceramics. It is within the ken of the art to select molds compatible with the polymer used to make the covering. For example, dip-coated polymer coverings should be easily removable from the molds without tearing or significant stretching.

Nanospun Coverings

In another embodiment, the coverings of the invention are biodegradable coverings for a breast implant which comprises a sheet, film or mat of nanofibers of one or more biodegradable polymer layers dimensioned and shaped to wrap or cover at least a portion of said breast implant. In this embodiment, when used as wraps, the biodegradable coverings have an outer surface and an inner surface and two peripheral edges. For example, nanofiber coverings can be cylindrically wrapped around the outer diameter of the breast implant and can overlay onto the convex front of implant or on the flat back of the implant to any degree desired by the surgeon. Such nanofiber coverings are typically soft and stretchable, making the covering quite flexible in the shapes and sizes into which it can be formed.

Nanofibers can be prepared by methods known in the art and can be woven, or non woven to form the sheet, film or mat. In a preferred method of preparing the nanofibers, a solution of polymer (optionally containing a drug) can be electrospun into a sheet or onto a mold. In such methods, the nanofibers consolidate to form the a fabric-like material. For example, U.S. Pat. No. 6,382,526 discloses a process and apparatus for the production of nanofibers useful in the present invention. Any method of forming nanofibers can be used. The properties of the sheet, mat or film produced by nanospinning is determined by the fiber-forming materials and/or by production parameters, such as voltage of electrodes in the electrospinning process, distance between high-voltage and low-voltage electrodes, rotational speed of the tubing (or of a core wire around which the tubing is manufactured), electrical field intensity, corona discharge initiation voltage or corona discharge current.

Thickness and Snugness

Any of the coverings of the invention can be multilayered or single layered. The overall thickness of the coverings ranges from about 25 μm to about 500 μm, from about 50 μm to about 300 μm, from about 100 μm to about 250 μm, and from about 80 μm to 120 μm. For multilayered coverings, each different layer can be successively applied to or over the previous layer. In some embodiments, an inner barrier layer is used to prevent diffusion or migration of drugs or other excipients from the covering into or onto the breast implant shell.

Certain physicomechanical properties of the coverings of the invention are similar to those of the implant shell. For example, at body temperature, both the shell and the covering are soft and malleable. The coverings are also elastomeric so that they can be stretched around the implant, or can be stretched and will shrink to fit snugly around the implant. Alternatively the covering can be made entirely of a fibrous, knit, woven, or non-woven construction to impart softness and flexibility so the breast implant can be placed inside a snug-fitting covering.

The coverings thus can fit with a tight degree of snugness around the implant, in a form fitting, almost clinging, way or can fit with a lesser degree of snugness, such as in a loose or draped manner. When looser fits are used the distance between the implant should be no more than a few millimeters, and preferably only 1-2 millimeters.

Biodegradable Polymers

The coverings of the invention are formed from biodegradable polymeric layers that optionally contain one or more drugs. Methods of making biodegradable polymers are well known in the art.

As used herein, a "biodegradable polymer" is a biocompatible polymer that is hydrolytically labile, oxidatively labile, or susceptible to enzymatic action, or any combination thereof, which action leads to the breakdown, whether partial or complete, of the polymer. It should be understood that polymers which are biodegradable have variable resorption times, which can depend, for example, on the nature and size of the breakdown products.

A biocompatible polymer is a polymer which is compatible with living tissue or a living system and is acceptable for use in or by animals or humans. Thus, a biocompatible polymer does not cause physiological harm to any significant or unacceptable degree, does not cause any or any significant amount of inflammation or immunological reaction, and is not toxic or injurious to the living tissue or system. For example, a biocompatible polymer can be ingested, implanted, placed on or otherwise used in a living subject or tissue without untoward effects.

Many biodegradable polymers are suitable for use in producing the coverings of the invention. In selecting polymers for use in the invention, the glass transition temperature (Tg) of the polymers, as well as the polymer-drug combination can be considered along with other parameters. For example, polymers with sufficiently low Tg can be pressed into films at low temperatures. Since some drugs may decompose at high temp, a low Tg polymer offers the ability to use thermal methods even in the presence of drugs. As used herein, low Tg polymers are those having a Tg below 40° C. The coverings of the invention that are films, e.g., as are prepared by dip coating, desirably have a Tg in the range of about 20° C. to about 30° C., but the range can vary from as low as about 10° C. up to about body temperature or even to about 40° C. These Tg values are for the final formulation of the covering (including polymer, drug or any other ingredient) as it is well known that adding excipients (e.g., drugs or plasticizers) to polymers can either lower or increase the Tg.

Hence, one way to assess whether a film has sufficient flexibility for use in the invention is to measure the elongation of the polymer. Suitable films have an elongation at yield between about 10% and about 400%, such that films are generally too stiff if elongation is below 10% and too pliable if above 400%.

Polymers with high glass transition temperatures tend to be stiff and if made into films, would be too stiff for use in the coverings for the breast implants in such a form. In such cases, incorporation of drugs can lower glass transition temperatures, making the stiffer polymers softer and more suitable for use. Alternatively, these high Tg polymers remain useful for the invention since they can be nanospun into felts for formation into a covering of the invention. Such felts render the covering soft even if the polymer itself may be stiff when formed into a film.

It is within the skill of the art to select polymers, drugs and processing methods to prepare the coverings of the invention.

Accordingly, biodegradable polymers suitable for use in the invention include but are not limited to:

polylactic acid, polyglycolic acid and copolymers and mixtures thereof such as poly(L-lactide) (PLLA), poly(D,L-lactide) (PLA), polyglycolic acid or polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL);

poly(oxa)esters, polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol (PEG), polyalkylene oxides (PAO), hydroxypropylmethylcellulose, polysaccharides such as hyaluronic acid, chitosan and regenerate cellulose, and proteins such as gelatin and collagen, and mixtures and copolymers thereof, among others as well as PEG derivatives or blends of any of the foregoing. All such polymers which provide the desired flexibility, pliability and/or softness to the coverings are contemplated for use to make the coverings of the invention.

In some embodiments, biodegradable polymers have diphenol monomer units that are copolymerized with an appropriate chemical moiety to form a polyarylate, a polycarbonate, a polyiminocarbonate, a polyphosphonate or other class of polymer.

For example, biodegradable tyrosine-derived polyarylates include those described in U.S. Pat. Nos. 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; as well as those described in U.S. Patent Application Publication Nos. 2002/0151668; 2003/0138488; 2003/0216307; 2004/0254334; 2005/0165203; and those described in PCT Publication Nos. WO99/52962; WO 01/49249; WO 01/49311; WO03/091337. These patents and publications also disclose other useful polymers containing tyrosine-derived diphenol monomer units or other diphenol monomer units, including polyarylates, polycarbonates, polyiminocarbonates, polythiocarbonates, polyphosphonates and polyethers.

Likewise, the foregoing patents and publications describe methods for making these polymers, some methods of which may be applicable to synthesizing other biodegradable polymers. Finally, the foregoing patents and publications also describe blends and copolymers with polyalkylene oxides, including polyethylene glycol (PEG). All such polymers are contemplated for use in the present invention.

Figure 6:
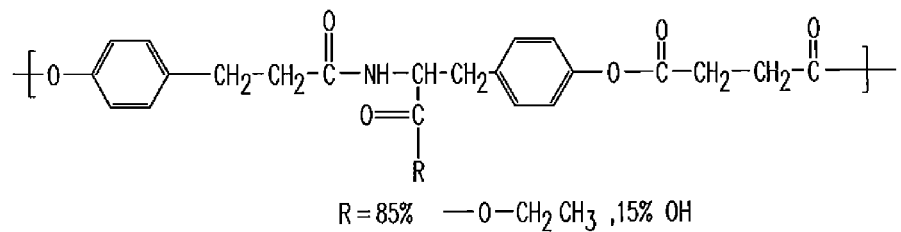
FIG. 6 depicts the chemical structures of the polymers in Table 1.
Figure 6:
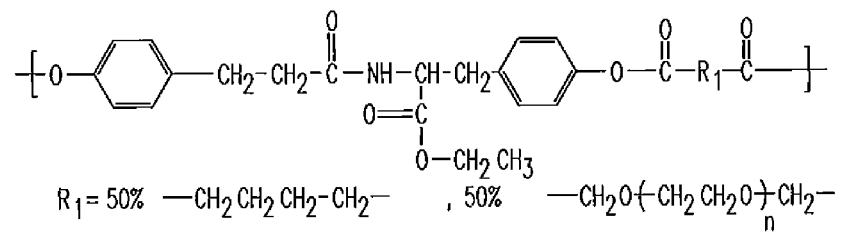
Figure 6:
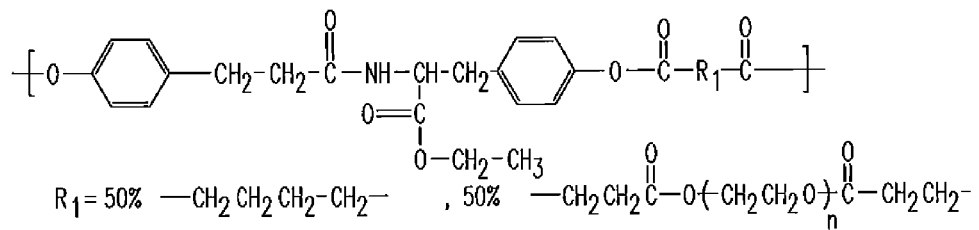

The representative structures for the foregoing polymers are provided in the above-cited patents and publications which are incorporated herein by reference as well as in the examples and in FIG. 6. Polyarylates are preferred because their physical characteristics can match those of silicone. Additionally, polyarylates are preferred because their range of Tg can be manipulated to form a film for coating an outershell of a breast implant.

Abbreviations used herein for naming polymers and the subunits thereof include B, 4-hydroxybenzoic acid; Bn or Bz, benzyl; D or DAT, desaminotyrosine or desaminotyrosyl; DATE, desaminotyrosine ethyl ester; E or Et, ethyl; glu, glutarate; M or Me, methyl; PEG, polyethylene glycol; Succ, succinate; and T, tyrosine.

As used herein, polymers based on diphenol monomer units have two part names. The first part identifies the diphenol moiety and the second part identifies the group with which the diphenol moiety is copolymerized. The names are written in the form poly(diphenol diacid), poly(diphenol carbonate), poly(diphenol iminocarbonate), etc.

The diphenol moiety is generally named for its three components, the two aromatic ring moieties and the tyrosine ester moiety. For example, DTE is desaminotyrosyl-tyrosine ethyl ester; DTBn is desaminotyrosyl-tyrosine benzyl ester. When a free acid is present (rather than an ester), the name for a third component is omitted. Thus, DT is the corresponding free acid form, namely desaminotyrosyl-tyrosine. BTE is the diphenol monomer 4-hydroxy benzoic acid-tyrosine ethyl ester; BT is the corresponding free acid form, namely 4-hydroxy benzoic acid-tyrosine.

The second part of the name identifies the group with which the diphenol moiety is polymerized, such as the diacid, the carbonate, the iminocarbonate and the like. Hence, specific examples include poly(DTE glutarate), poly(DTBn carbonate) and the like.

If a mixture of diphenol moieties or of copolymerized groups (such as two diacids) are present in the polymer, then that part of name may includes the designation "co" or may have a hyphen, along with an indication of percentage of one of the two moieties. For example, poly(DTE:10DT-co-succinate) and poly(DTE-10-DT succinate) are used interchangeably to mean a polymer made by copolymerizing a mixture of 90% desaminotyrosyl-tyrosine ethyl ester and 10% desaminotyrosyl-tyrosine with the diacid succinic acid. An example of a mixed diacid is poly(DTE-co-50:50 PEG-bis-succinate adipate).

Additional preferred polyarylates are random copolymer of desaminotyrosyl-tyrosine (DT) and an desaminotyrosyl-tyrosine ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of polyarylates are similar to the foregoing but the desaminotyrosyl moiety is replaced by a 4-hydroxybenzoyl moiety. Preferred DT or BT contents include those copolymers with from about 1% to about 30%, from about 5% to about 30% from about 10 to about 30% DT or BT. Preferred diacids (used in forming the polyarylates) include succinic, glutaric, sebacic, adipic and glycolic acid as well as PEG or other PAOs and polyethylene glycol diacids such as the polyethylene glycol-bis-alkyl diacids described in U.S. Pat. No. 7,271,234.

Additional biodegradable polymers useful for the present invention are the biodegradable, resorbable polyarylates and polycarbonates disclosed in U.S. provisional application Ser. No. 60/733,988, filed Nov. 3, 2005 and in its corresponding PCT Appln. No. PCT/US06/42944, filed Nov. 3, 2006. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate and DT PEG ester succinate.

Useful tyrosine-derived polyarylates are the DTE-DT succinate family of polymers, e.g., those polymers having from 0-50%, 5-50%, 5-40%, 1-30% or 10-30% DT, including but not limited to, about 1, 2, 5, 10, 15, 20, 25, 27.5, 30, 35, 40%, 45% and 50% DT.

Additionally, the polyarylate polymers used in the present invention can have from 0.1-99.9% PEG groups or PEG diacid groups (see the bottom polymer of FIG. 6) to promote the degradation process as described in U.S. provisional application Ser. No. 60/733,988.

Further biodegradable polymers useful in the present invention are the dihydroxybenzoic acid (DHB)-based polymers described in U.S. provisional application Ser. No. 60/915,673, filed May 2, 2007, and include copolymers and blends of the DHB-based polymers with any of the biodegradable polymers described herein. For example, the DHB-based polymers can have a mixture of DHB esters and DHB free acids polymerized with a diacid or other compatible moiety. Similarly, the DHB-based polymers can be polymerized with a mixture of diacids such as succinic, glutaratic or adipic acid with a PEG bis-succinate, PEG bis-glutarate or PEG bis-adipate. A PEG bis-succinate diacid is shown in FIG. 6, bottom polymer. All such combinations are contemplated as well as copolymerization with polyalkylene oxides as shown. e.g., in U.S. Pat. No. 5,658,995 or 6,120,491.

Some polyarylates have inherent microtexturing, which is desirable in forming the temporarily-textured outer surface on the breast implant. This inherent microtexturing, without being limiting to a particular theory, occurs as a result of several different mechanisms. First, the polyarylate backbone may be considered to consist of a hard segment (the aromatic units) and a soft segment (the aliphatic diacid units). Polymers with hard and soft units are known to phase separate, which leads to microdomains having different textures. Second, polyarylate side-chains can be selected based on their flexibility properties. Side-chains with different flexibility than the polyarylate backbone may phase separate from the polyarylate backbone leading to microdomains with different structures and different textures. Third, copolymerization of the polyarylate, which is relatively hydrophobic, with polymers that are hydrophilic, can lead to phase separation into relatively hydrophobic and hydrophilic domains. Finally, formulations of polyarylates with drugs that are relatively insoluble with polyarylates can lead to phase separations and microdomain formation.

Microtexturing can also be created by blends of two different polymers with different water contact angles.

Polymers contemplated for use in the invention include, but are not limited to, 1) p(85:15 DTE:DT-co-succinate)
2) p(90:10 DTE:DT-co-adipate)

-continued 3) p(DTE-co-50:50 PEG400 bis-succinate:adipate)
4) p(DTE-co-50:50 PEG600 acid:adipate)
5) p(DTE-co-10:90 PEG600 acid:adipate)
6) p(DTE-co-10:90 PEG400 acid:adipate)
7) p(DTE-co-30:70 PEG400 bis-succinate:adipate)
8) p(70:30 DTE:PEG alcohol-co-glutarate)
9) p(DHB methyl ester-co-glutarate)
10) p(85:15 DHB methyl ester:DHB-co-glutarate)
11) p(85:15 DHB benzamide:DHB-co-glutarate)
12) p(DHB methyl ester-co-15:85 PEG400 bis-glutarate:glutarate)

Blends contemplated for use in the invention include, but are not limited to, blends of the polymers (1)-(12) listed above include a 50:50 blend of polymers 1 and 4, a 50:50 blend of polymers 2 and 3, a 50:50 blend of polymers 3 and 5, a 20:80 blend of polymers 9 and 12, a 20:80 blend of polymers 10 and 12 and a 20:80 blend of polymers 11 and 12.

Layers

In accordance with the invention, the coverings have one or more biodegradable polymeric layers. The arrangement of layers in the coverings can vary by embodiment. Each layer can be formed from one or more dips, coatings or application of a polymer solution, or formation of nanofibers. Each layer can optionally contain one or more biologically active agents. For example, the coverings of the invention can have (a) a single or multiple smooth polymer layers; (b) a single or multiple textured polymer layers; (c) an inner barrier layer and an outer, smooth polymer layer; (d) an inner barrier layer, a middle polymer layer, and an outer textured polymer layer. Any variation on this is contemplated.

In some embodiments, the coverings of the invention have an inner, bioabsorbable barrier layer. This layer can prevent any drugs, excipients or polymer degradation products in the one or more central and/or outer layers of the covering from migrating or diffusing into the shell of the breast implant (which could lead to rupture or compromise of the shell). The barrier also can direct any active ingredients into the surrounding tissue. Barrier layers also can be used in the absence of any drugs in the outer layers.

Suitable barrier coating materials include water-soluble polymeric, biodegradable pharmaceutical excipients, including but not limited to, acacia, agar, albumin, alginic acid, ammonium alginate, calcium alginate, carbomer, carboxymethylcellulose, cargeenan, ceratonia, chitosan, crosmellose sodium, gelatin, guar gum, hydroxyethylcellulose, hydroxyethylmethyl cellulose, starch, hydroxypropylstarch, methyl cellulose, pectin, polycarbophil, polydextrose, gantrez, polyvinyl alcohol, polyvinyl acetate phthalate, potassium alginate, propylene glycol alginate, sodium starch, tragacanth, xanthan gum, glycolate, pregelatized starch, as well as the pharmaceutically acceptable salts of any of the foregoing.

The barrier layers should be resistant to penetration by organic solvents to allow compatibility with the use of solvents used in preparing the other polymeric layers of the coverings. The barrier layers should also be resistant to drug leaching. Drug leaching usually occurs when very hydrophobic drugs migrate into similarly hydrophobic polymers such as silicone. Therefore, preferred barriers are usually highly hydrophilic and soluble in water. Preferred polymers for the barrier layer which are impermeable to tetrahydrofuran (THF) and methylene chloride include hydroxyethylcellulose, sodium carboxymethylcellulose, xanthan gum, Carbopol 971P NF, Carbopol 974P NF and polyvinyl alcohol.

Drugs

Any drug, biological agent, or active ingredient that is compatible with the process of preparing the coverings of the invention can be incorporated in to one or more of the polymeric biodegradable layers.

Furthermore, any drug or biologically-active agent desired for delivery to the surgical site during implantation can be formulated into one or more of the polymeric layers of the covering. Doses of such drugs and agents are known in the art. Hence, those of skill in the art can determine the amount of drug or agent desired for delivery, and calculate the amount of that should be loaded into the polymeric layers of the coatings for a breast implant of a particular volume. For example, the breast implants can be modeled as half spheres or quarter spheres with a thin covering of known thickness.

Drug elution times can be determined based on the drug and its time course of action, which generally are over the course of 3 to 100 days. For example, antibiotic activity for 7-10 days (or more) can be sufficient to prevent or reduce colonization of implants, thereby preventing or reducing capsular contracture (or its overall incidence as could be assessed, for example, in a clinical trial).

In accordance with the invention, the drugs and biologically-active agents for formulation into the polymeric layers of the coverings include, but are not limited to, anesthetics, antibiotics (aka antimicrobials or antibacterials), anti-inflammatory agents, fibrosis-inhibiting agents, anti-scarring agents, leukotriene inhibitors/antagonists, cell growth inhibitors and the like.

As used herein, "drugs" is used to include all types of therapeutic agents, whether small molecules or large molecules such as proteins, nucleic acids and the like. The drugs of the invention can be used alone or in combination.

Examples of non-steroidal anti-inflammatory agents include, but are not limited to, Acetominophen, aspirin, celecoxib, diclofenac, diflunisal, flurbiprofen, ibuprofen, indomethacin, ketoprofen, ketorolac, meclofenamate, meloxicam, methyl salicylate, nabumetone, naproxen, oxaprozin, piroxicam, sulindac, tolmetin and trolamine.

Examples of anesthetics include, but are not limited to, lidocaine, bupivacaine, mepivacaine and xylocaine. Local anesthetics have weak antibacterial properties and can play a dual role in the prevention of acute pain and infection.

Examples of antimicrobial drugs include, but are not limited to, aminoglycosides such as amikacin, gentamicin, kanamycin, neomycin, streptomycin, and tobramycin;

antibiotics such as bacitracin, clindamycin, daptomycin, lincomycin, linezolid, metronid, polymyxin, rifaximin, vancomycin;

cephalosporins such as cephazolin;

macrolide antibiotics such as erythromycin, azithromycin and the like;

β-lactam antibiotics such as penicillins;

quinolones such as ciprofloxacin;

sulfonamides such as sulfadiazine;

tetracyclines such as minocycline and tetracycline; and other antibiotics such as rifampin, triclosan and chlorhexidine.

Other drugs that can be incorporated into the polymeric layers of the coverings of the invention, include, but are not limited to, keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, nicotinic acid, chemodeoxycholic acid, chlorambucil and anti-neoplastic agents such as paclitaxel, sirolimus, 5-flurouracil and the like. Other drugs include those that act as angiogenensis inhibitors or inhibit various growth factors such as epidermal growth factor, PDGF, VEGF, FGF (fibroblast growth factor) and the like. These drugs include anti-growth factor antibodies (neutrophilin-1), growth factor receptor-specific inhibitors such as endostatin and thalidomide.

Preferred antimicrobial agents of the invention include rifampin, minocycline, gentamicin, vancomycin, triclosan, alone or in combination. Rifampin and minocyline are a preferred combination of anti-microbial agents.

Examples of leukotriene inhibitors/antagonists include, but are not limited to, leukotriene receptor antagonists such as acitazanolast, iralukast, montelukast, pranlukast, verlukast, zafirlukast, and zileuton.

Another drug that can be incorporated into the coverings of the invention is sodium 2-mercaptoethane sulfonate (Mesna) which has been shown to reduce capsule formation around implants in rabbits [Ajmal et al. (2003) Plast. Reconstr. Surg. 112:1455-1461]. Other drugs that reduce capsule formation can be incorporated into the coverings of the invention.

Assembly of Covering and Breast Implant

After manufacture, the coverings of the invention can be packaged and sterilized for assembly onto a breast implant immediately prior to surgery. Alternatively, the coverings of the invention can be assembled onto the breast implant, packaged and sterilized at the time of manufacture so that a completed breast implant assembly is delivered to the surgical suite. In any event, clean, sterile gloves and/or atraumatic instruments should be used when handling the coverings.

The coverings of the invention can be prepared for breast implant insertion by several different methods. For example, the covering can be delivered sterile and pre-expanded on a prosthetic form such as an expanded balloon or other support. Immediately prior to use, the balloon is deflated or the support otherwise altered so the expanded shell can be removed, and the breast implant placed into the covering with the convex (frontal) side of the implant fully covered and the fill side of the implant facing the covering's insertion hole. Such an embodiment would minimize the amount of handling of the cover needed during surgery.

Alternatively, the covering can be delivered to the surgeon unexpanded when the covering has at least one glass transition temperature at, close to, or near 37° C. In this case, the covering can be stretched by aseptically grasping the covering in both hands with fingers inside the insertion hole and gently stretching the hole into a wider configuration prior to inserting an implant.

As another alternative, coverings can be gently warmed in a sterile saline bath (irrigating solution) prior to stretching and insertion of the implant or in an oven provided sterile or aseptic conditions are maintained. Coverings with glass transition temperatures near room temperature should return to conforming to the implant on their own once the implant is properly placed within the covering. The covering can be further manipulated around the implant with gentle probing and/or kneading of the covering/implant combination. Immersing a smooth implant in sterile saline for a few seconds can also facilitate placement of the implant inside the covering as it provides a slippery surface that allows the covering to glide more easily around the implant.

For example, a covering of approximately 100 micron thickness and approximately 12 cm diameter with an insertion hole of approximately 5 cm can be gently stretched by grasping two sides of the insertion hole and pulling in opposite directions for 15-30 seconds. The covering is then rotated 90 degrees and the process repeated until the insertion hole is approximately 7-10 cm wide. For this size covering, a smooth implant of 300 cc or 340 cc is pushed into the covering insertion hole by grasping two opposite sides of the implant in one hand while holding the covering open with the other. The implant can be aligned within the covering using finger probing of the implant inside the covering followed by smoothing of the convex outer surface of the covering. Once the covering is placed onto the implant, the combination can be placed into warm irrigation solution to facilitate shrinking and form-fitting of the covering around the implant.

Once form-fitted with a covering, the implant assembly can be inserted into the patient using standard breast reconstructive or augmentative surgical techniques. Breast reconstruction usually occurs following complete mastectomy but can be also be done for congenital deformities or trauma injury to the breast. Breast augmentation is typically done by women for cosmetic reasons. However, the coverings of the invention can be used with breast implants in connection with transgender surgery.

Additional Aspects

Another aspect of the invention is directed to a kit comprising a breast implant and any of the biodegradable covering of the invention. The kits optionally contain instructions for inserting the accompanying implant into the covering. The coverings in the kit are size matched to the implant supplied with the kit. The kits are sterile. At the time of surgery, the kits are opened and the implant is inserted in the covering as described herein.

Alternatively, the kit can consist of a breast implant assembly of the invention. Such assemblies comprising any one of the biodegradable coverings of the invention containing or wrapped around a breast implant. As with the foregoing kits, the coverings and implants of the assembly are appropriately sized matched.

A further aspect of the invention is directed to a method for reducing post-surgical complications from breast augmentation, breast reconstruction or breast restoration in a subject which comprises surgically implanting a breast implant assembly of the invention into the subject. The present assemblies are used in standard surgical breast augmentation, reconstruction or restoration procedures and do not lead to any major changes or complications in those procedures. In fact, if such assemblies of the invention need to be replaced in a follow on procedure, such as can happen when the implant shell deflates or ruptures, the procedure should be facilitated as the implant shell should have little or no tissue in growth and should be more easily removable than shells that did not initially have a covering in accordance with the invention.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety.

Example 1

Polymer Synthesis

The polymers used in Examples 2-5 and 9-11 are listed in Table 1 and the structures thereof are shown in FIG. 6.

TABLE 1

| Blend | Polymer 1 | Polymer 2 |
|---|---|---|
| 1 | p(DTE:15% DT-co-succinate) | p(DTE-co-(50:50 PEG 600 acid:adipate)) |
| 2 | p(DTE:10% DT-co-adipate) | p(DTE-co-(50:50 PEG 400 bis-succinate:adipate)) |
| 3 | p(DTE-co-(50:50 PEG 400 bis-succinate:adipate)) | p(DTE-co-(10:90 PEG 600 acid:adipate)) |

These polymers, and tyrosine-derived diphenol polyarylate polymer in general, were synthesized as generally described in U.S. Pat. Nos. 5,216,115 and 5,597,507 using a carbodimide-mediated coupling reaction. Briefly, equimolar amounts of the diol and diacid were condensed in methylene chloride using diisopropyl carbodimide as the coupling agent in the presence of dimethylaminopyridine and paratoluenesulfonic acid catalysts. For those polyarylates which contain a free acid moiety, a similar synthesis was conducted followed by hydrogenation as described in U.S. Pat. No. 6,120,491. The polymers were usually isolated by repeated precipitation from isopropanol.

As an illustrative example for synthesis of p(DTE:15%DT-co-succinate), a mixture of 85% DTE and 15% DTBn was condensed with an equimolar amount of succinic acid. After polymerization was complete, the polymer was hydrogenated to covert the tyrosine benzyl esters to free acids and yield p(DTE:15%DT-co-succinate). In an example with mixed diacids, p(DTE-co-50:50 PEG 400 bis-succinate:adipate) was synthesized by condensing a 50:50 mixture of PEG 400 bis-succinate and adipic acid with an equimolar amount of DTE.

Example 2

Preparation of Breast Implant Coverings: Molding

Polymer blends were prepared by mixing 10 g of Polymer 1 and 10 g Polymer 2 from Table 1 in 180 mL tetrahydrofuran (THF) and 20 mL of methanol (MeOH) to yield a 10% (w/v) solution with the polymers in 1:1 ratio (w/w). After the polymers were dissolved, 1.1 g rifampin and 1.1 g minocycline were added to each solution and mixed well. Polypropylene or delrin molds in the shape of a breast implant were fixed onto a holder and dipped slowly into and slowly out of the solution using a dipping machine from DipTech Systems, Inc. Five dips were applied to each mold with 60 min intervals between each successive dip. The dipped molds were dried at room temperature for 24 h followed by drying in a 55° C. oven for 16 h. After drying, the molded polymer solution produced a breast implant covering that was easily peeled from the mold.

Example 3

Drug Release Studies

Films of polymer blends were prepared for drug release studies by mixing 1 g Polymer 1 and 1 g of Polymer 2 from Table 1 in 15 mL methylene chloride. After the polymers dissolved, 0.2 g of rifampin and 0.2 g of minocycline were added and mixed well. The solution was poured onto a TEFLON coated glass surface and spread to 0.25 mm with a spreading knife. The film was covered by an aluminum foil wrapped glass dish and dried at room temperature overnight. The film was peeled off and put in an amber bag and dried in a vacuum oven at 25° C. for 3 days. The dried film was cut into small pieces of about 10 mg and placed into a 20 mL vial containing 10 mL of PBS. Aliquots of buffer were removed periodically for analysis and replaced with fresh buffer. Samples were analyzed by HPLC to determine the cumulative amount of released rifampin and minocycline.

Figure 7:
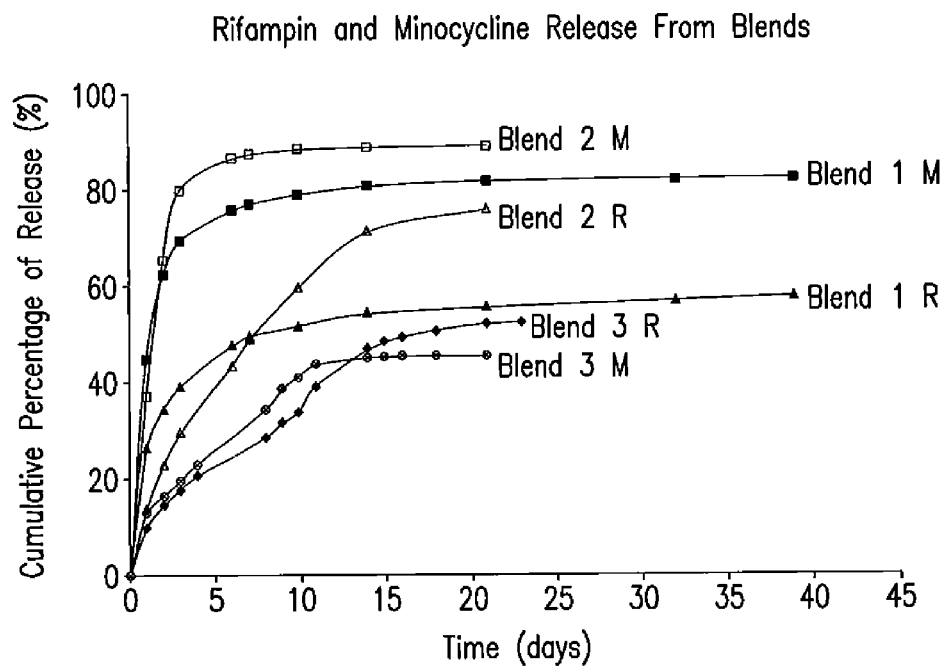
FIG. 7 graphically illustrates the cumulative percentage release of rifampin and minocycline from the polymer blends as provided in Example 2.

With these blends, from about 40% to about 85% of the minocycline was released within 15 days and from about 45% to about 70% of rifampin was released within 20 days (FIG. 7).

Example 4

Covering Thickness

Figure 8:
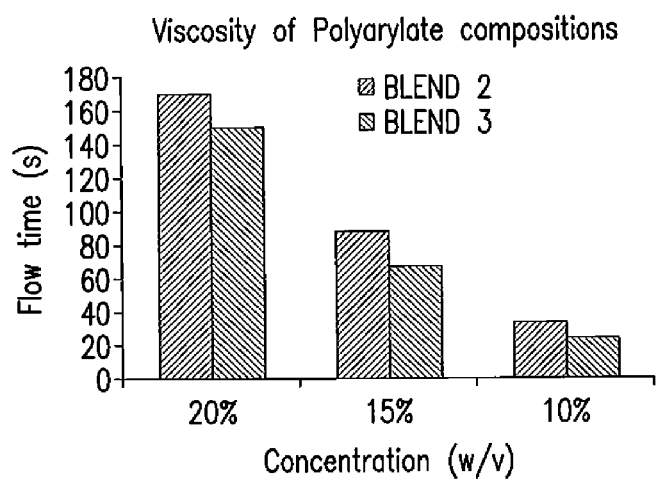
FIG. 8 graphically illustrates the viscosity of Blend 2 of the invention as a function of polymer concentration as described in Example 3.

The thickness of a layer depends on viscosity, which in turn depends on polymer concentration in the dipping solution. The viscosity of Blend 2 and Blend 3 was determined for solutions with a 1:1 ratio of polymers at a total concentration of 10%, 15% or 20% (w/v) in 9:1 THF:MeOH. The results in FIG. 8 show that viscosity (measured as flow time at 72° F.) increases with polymer concentration.

Figure 9:
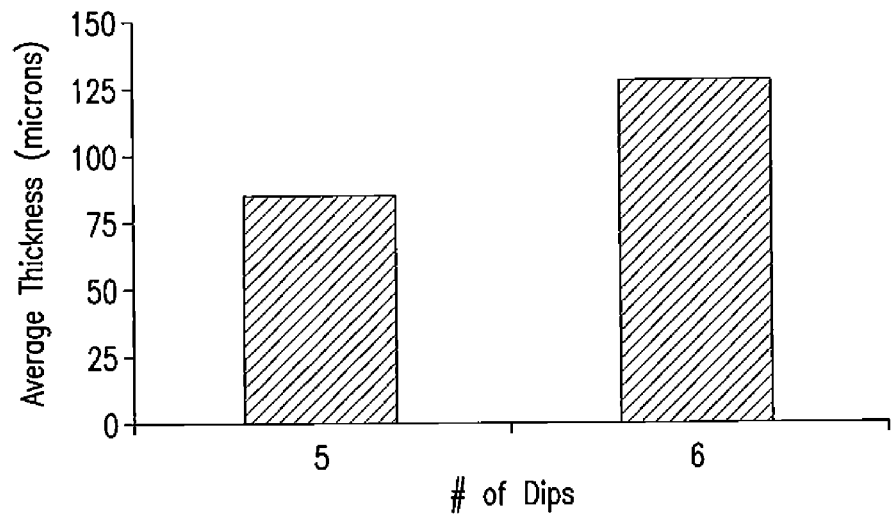
FIG. 9 graphically depicts the thickness of the polymer layer for Blend 2 as a function of dips as described in Example 3.

Thickness of the covering can be increased by increasing the number of dips. A solution of 10% Blend 3 in 9:1 THF:MeOH was prepared. The solution was used to produce coverings by multiple dips and drying as described in Example 2. FIG. 9 shows that the coverings prepared with five dips were about 80-85 µm whereas coverings prepared with six dips were at least about 125-130 µm thick.

Example 5

Textured Breast Implant Covering: Molding

Coverings were prepared using the Blend 1 and drugs as described in Example 2, except that 1.1 g camphor was added to the polymer-drug solution. The camphor was allowed to fully dissolve before proceeding to dip the molds in the solution. After drying at 55° C., the molds were dried under vacuum at 30° C. for 48 h, during which time the camphor sublimed, leaving behind a textured surface. The covering were easily peeled from the mold.

Example 6

Textured Breast Implant Covering: Layered Molding

Coverings were prepared using Blend 1 and drugs as described in Example 2 and four (4) dips were applied to the mold. A polymer-drug solution with camphor was also prepared as described in Example 4 and the coated molds was dipped one time into the camphor-polymer-drug solution. Drying proceeded as in Example 4, namely for 24 h at room temperature, in a 55° C. oven for 16 h and under vacuum at 30° C. for 48 h. Again, the camphor sublimed, leaving behind a textured surface. The covering were easily peeled from the mold.

Example 7

Preformed Textured Breast Implant Covering: Electrospinning

A mat of polyarylate fibers are prepared by electrospinning a solution of 8 g DTE:27.5 DT succinate, 1 g rifampin and 1 g minocycline in 50 mL chloroform onto a mandrel (2.5 inches×3 inches×0.5 inches) under conditions that produce nanofibers, for example, as described by Subbiah et al. (2005) J. Appl. Poly. Sci. 96: 557-569. After drying, the mat is removed and shaped to provide a breast implant covering.

Example 8

Wrapped Textured Breast Implant Covering: Electrospinning

A flat 200 µm thick mat was prepared as described in Example 7 except that the polyarylate fibers were spun onto a flat surface. A 3"×5" piece was cut from the mat for wrapping around a breast implant.

Example 9

Dosing

The amount of drug needed to prepare a dipping solution that will produce a breast implant covering capable of delivering a particular drug dose was calculated for breast implants of varying volumes by approximating a round breast implant as a spherical cap representing a ½ or ¼ sphere. Hence, a round implant having a volume of 125 cm$^3$ and a spherical radius of 3.9 cm has a surface area of 144 cm$^2$ in the ½ sphere model, whereas in the ¼ sphere model, the surface area is 182 cm$^2$ and the calculated spherical radius is 5.8 cm. A 100 µm thick implant covering for a 125 cm$^3$ volume implant covering prepared with 10% drug in the polymer matrix would have 187 mg drug in the ½ sphere model and a 300 µm thick implant would have 561 mg drug.

Example 10

Gentamicin Release from Textured Samples

Gentamicin-containing textured polymer samples were prepared using solvent casting techniques. For these studies, solutions/suspensions were prepared as follows: Sample 1: 0.4 g DTE:10% DT succinate and 100 mg gentamicin (GM) in 4 mL 1,4-dioxane; Sample 2: 0.3 g DTE:10% DT succinate, 75 mg GM and 1 g Camphor in 6 mL 1,4-dioxane; and Sample 3: 0.3 g DTE and 7 g NaCl were mixed in 3 mL 1,4-dioxane and 0.3 mL water. The solution/suspensions were solvent cast and dried to form films. After Sample 3 was partially dried, the NaCl was removed by soaking the film in 4 L of cold water, changed hourly, until the AgNO$_3$ test was negative. The film was then loaded with GM by pumping a solution of 75 mg/mL GM in water through the film followed by complete drying.

GM release was determined as a function of time by incubating a equal size pieces of Samples 1-3 in PBS at 37° C., periodically sampling the solution and assaying for GM content. GM content was determined by a spectrophotometric assay by mixing 1:1:1 aliquot, isopropanol and reagent solution. Absorbance was measured between 10 and 40 minutes after mixing at 332 nm using a polystyrene cuvette. The reagent solution consisted of 2.5 g o-phthaldialdehyde, 62.5 ml methanol, 3 ml 2-mercaptoethanol and 560 ml 0.04 M sodium tetraborate in distilled water.

Figure 10:
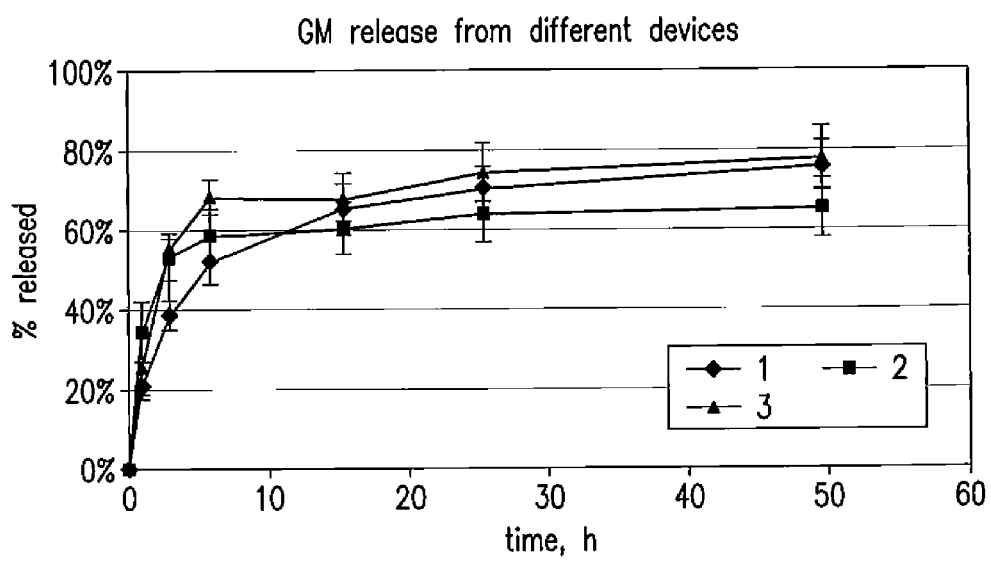
FIG. 10 graphically illustrates the percentage of gentamycin released from textured polymer films as described in Example 9.

The amount of GM in Samples 1-3 was 20.65%±3.85%, 15.60%±1.13% and 46.04%±11.85%, respectively. Sample 1 has microtexturing, Sample 2 has microtexturing and pores 2 (left after from the camphor sublimation) and Sample 3 has microtexturing and pores (left from the salt leaching). The rate and overall percentage of GM released was similar for all three samples (FIG. 10).

Example 11

Breast Implant Covering with a Barrier Layer

A 5% solution of hydroxyethylcellulose (HEC) in water was prepared by dissolving 10 g of HEC in 200 ml water. Silicone molds in the shape of a breast implant were fixed onto a holder and dipped slowly into and slowly out of the solution. Four dips were applied to each mold with 30 min intervals at 50° C. between each successive dip. The dipped molds were dried overnight at 50° C.

Blend 3 was prepared by mixing 10 g of Polymer 1 and 10 g Polymer 2 from Table 1 in 180 mL tetrahydrofuran (THF) and 20 mL of methanol (MeOH) to yield a 10% (w/v) solution with the polymers in 1:1 ratio (w/w). After the polymers were dissolved, 0.55 g rifampin and 0.55 g minocycline were added to each solution and mixed well. Silicone molds, pre-coated with HEC as described above, were fixed onto a holder and dipped slowly into and slowly out of the solution. Five dips were applied to each mold with 15-20 min intervals between each successive dip. The dipped molds were dried overnight at room temperature and then for 24 h at 50° C. After drying, the molded polymer solution produced a breast implant covering with an HEC barrier layer and an antibiotic-containing biodegradable layer that was easily peeled from the mold. The clear silicone mold remained clear (no yellow coloring), indicating that the HEC layer had served as a barrier preventing diffusion of the drugs into silicone.

Example 12

ZOI Antibiotic Activity in Anti-Microbial Covering

Polymer Blend 3, rifampin and minocycline were used to prepare coverings for rabbit-sized silicone breast implants (approximately 3 cm diameter) as described in Example 2 using an appropriately sized mold (mandrel). Disks of 1 cm diameter were cut from the coverings.

Antibiotic activity against clinical and/or lab isolates of various bacteria was assessed for the polymer films using the Kirby-Bauer test for antibiotic susceptibility. The tested bacteria included *Staphylococcus epidermidis* (methicillin resistant, clinical isolate), *Staphylococcus aureus* (methicillin resistant), *Enteroccus faecalis* (vancomycin resistant) and *Escherchia coli*.

Stock cultures were transferred to tryptic soy agar (TSA) and incubated aerobically at 37° C. for 18-24 h before harvesting for use. Several colonies were removed from the TSA plate with a sterile swab and inoculated into sterile PBS until the turbidity reached McFarland #0.5 standard. Plates were prepared by performing lawn streaking (three cross streaks) on Mueller-Hinton II agar (MHA) and allowed to dry for 10-15 min before use.

Disks were dipped in sterile saline at 37° C. for 1 min, firmly pressed into the center of pre-warmed MHA plates (one disk per plate; in triplicate for each film) and incubated at 37° C. Pieces were transferred every 24 h to fresh, prewarmed MHA plates using sterile forceps. The distance from the sample to the outer edge of the inhibition zone (ZOI) was measured every 24 h. Table 2 provides the results; ZOI greater than 5-6 indicate the bacteria were susceptible to the antibiotic.

TABLE 2

| Bacteria | ZOI (day 1) (mm) | ZOI (day 4) (mm) | ZOI (day 7) (mm) |
| --- | --- | --- | --- |
| *S. epidermidis* | 40 | 38 | 33 |
| *S. aureus* | 44 | 37 | 36 |
| *E. faecalis* | 40 | 32 | 26 |
| *E. coli* | 20 | 16 | 17 |

Example 13

Rabbit Implants

The efficacy of a covering in preventing infection was assessed in a rabbit model. In brief, covered breast implants and controls were surgically implanted in rabbits, inoculated directly with *S. aureus* bacteria in the implant pocket and assessed for infectivity and inflammation as described below.

Polymer Blend 3, rifampin and minocycline were used to prepare coverings for rabbit-sized silicone breast implants (approximately 3 cm diameter) as described in Example 2 using an appropriately sized mold (mandrel).

Bacterial Inocullum Preparation

On the day before surgery, liquid *S. aureus* cultures were prepared from a frozen stock by growing 80 μL thawed stock in 20 mL trypticase soy broth at 37° C. in water bath overnight with shaking (4 stocks). The overnight cultures were combined into two 50 mL conical tubes (40 ml/tube), centrifuged and the bacterial pellet resuspended in 20 mL fresh, sterile saline. Concentrations were determined by spectrophotometry and confirmed by colony forming units (CFU) per mL on TSA plates. The bacterial suspensions were diluted as need for delivery of 1 mL of the culture per implant rabbit to be implanted, and an aliquot plated on TSA plates to confirm CFU/mL.

Surgery

Rabbits were divided into three groups of three to receive a control implant, a control implant irrigated with a solution of 20% betadine in saline, or an implant with the anti-microbial covering. Each animal had a subcutaneous pocket created surgically through the thoracic part of the trapezius muscle on each side of the spine, and thus each rabbit received two implants. A separate incision was created through which a catheter was tunneled into the pocket for bacterial inoculum delivery. One device was placed per pocket, and the pocket was surgically closed. After closure, a dose of *S. aureus* was delivered into the pocket through the catheter, the catheter withdrawn, and the incision closed via purse string suture. Animals were allowed to recover and were maintained out to 7 days following surgery. After 7 days, blood was drawn animals were euthanized, and the pockets were aseptically opened.

Devices were explanted and placed in a saline/Tween buffer (0.5% Tween-80) and bacteria recovered from the device as described below. The pocket was swabbed with sterile swabs and cultured to assess bacterial growth.

Bacterial Recovery

The explanted devices were placed in sufficient volume of sterile saline/Tween buffer to cover the device, vortexed 15 seconds and sonicated for 5 minutes. Those devices were transferred to a fresh container with the same volume of sterile saline/Tween buffer, vortexed for 30 seconds and sonicated 5 minutes. The sonicated solutions were serially diluted and plated on TSA plates to determine CFU. The blood samples were cultured to assess septicemia.

Histology

The tissue surrounding implant was excised at necropsy, placed in formalin, and processed for routine histological analysis using hematoxylin and eosin (H&E) stain.

Results

In the control and betadine controls, 23/24 sites showed evidence of infection by visual examination for pus at the time of explants in the pocket or on the device. Pocket and device were counted as separate sites. None of the sites (12) that received the anti-microbial covering showed any pus in the pocket or on the device.

Figure 11:
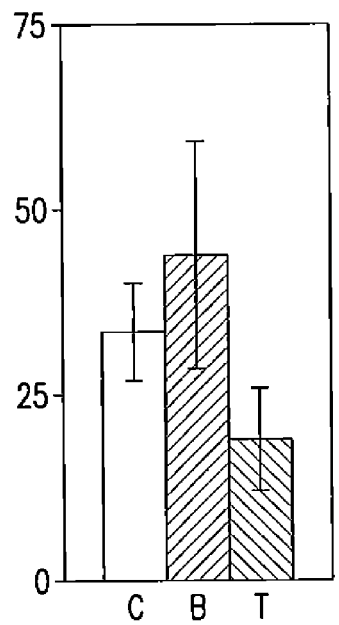
FIG. 11 graphically illustrates the inflammatory response surrounding explanted breast implants with no treatment or covering (C), with betadine irrigation at the time of implant but no covering (B) and with an anti-microbial covering (T). The scale is arbitrary.

Inflammation at the site was assessed by eryththema and edema scores and is shown in FIG. 11, where the inflammatory response surrounding explanted breast implants is (C) no treatment or covering, (B) betadine irrigation at the time of implant but no covering and (T) an anti-microbial covering. The scale is arbitrary units, with 0 being no inflammation, 25 being little inflammation, 50 being mild inflammation, 75 being moderate inflammation and 100 being significant inflammation. The difference in the inflammatory response between the control and betadine control groups relative to the anti-microbial covering group is statistically significant. The difference in the inflammatory response with the two control groups is not statistically significant.

Figure 12:
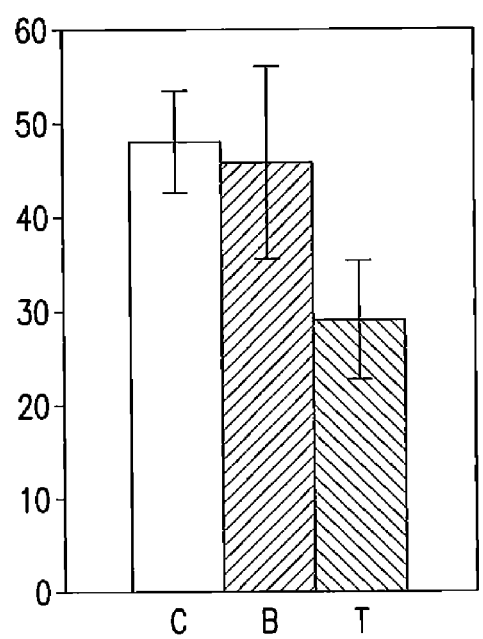
FIG. 12 graphically illustrates capsule surrounding explanted breast implants with no treatment or covering (C), with betadine irrigation at the time of implant but no covering (B) and with an anti-microbial covering (T). The scale is arbitrary.

Additionally, capsule formation was reduced in the anti-microbial covering group (FIG. 12) for the same set of samples as depicted in FIG. 11 (i.e., groups C, B and T). The scores measure thickness and opacity of the capsule in arbitrary units with 0 being no capsule, 25 being a little capsule/thickness/opacity, 50 being mild capsule/thickness/opacity, 75 being moderate capsule/thickness/opacity and 100 being significant capsule/thickness/opacity.

We claim:

1. A biodegradable covering for a breast implant, said biodegradable covering comprising one or more biodegradable polymer layers with elastomeric properties said biodegradable covering having a $T_g$ of less than about 40° C., and an outer surface, an inner surface for non-adherent contact with an outer surface of said breast implant, and a flexible opening allowing insertion of said breast implant through said flexible opening into said biodegradable covering such that when said breast implant is disposed within said biodegradable covering said inner surface of said biodegradable covering is in contact with but not adhered to said breast implant, said one or more biodegradable polymer layers include one or more drugs consisting of antimicrobial agents, and at least one of an anesthetic and anti-inflammatory agent.

2. The biodegradable covering of claim 1, wherein said antimicrobial agent is selected from the group consisting of rifampin, minocycline, gentamicin, vancomycin, triclosan, novobiocin, cephalosporin, alone or in combination.

3. The biodegradable covering of claim 1, wherein said one or more drugs are rifampin and minocycline.

4. The biodegradable covering of claim 1, wherein said anesthetic is selected from the group consisting of lidocaine, bupivacaine, mepivacaine and xylocaine.

5. The biodegradable covering of claim 1 including a plurality of said biodegradable polymer layers, and wherein the layer forming said inner surface of said biodegradable covering is a drug impermeable, biodegradable barrier layer capable of preventing one or more drugs from contacting the breast implant when the breast implant is disposed within said biodegradable covering.

6. The biodegradable covering of claim 1, wherein said outer surface of said biodegradable covering is smooth or textured.

7. The biodegradable covering of claim 1, wherein said biodegradable covering is substantially encasing said breast implant.

8. The biodegradable covering of claim 1, wherein said biodegradable covering is dimensioned and shaped to form fit a round, teardrop or contoured shaped breast implant therein.

9. The biodegradable covering of claim 1, wherein one or more of said biodegradable polymer layers is constructed from a tyrosine-derived polyarylate.

10. The biodegradable covering of claim 1, wherein one or more of said biodegradable polymer layers is a synthetic tyrosine-containing polymer.

11. The biodegradable covering of claim 1, wherein one or more of said biodegradable polymer layers comprises a blend of polymers.

12. The biodegradable covering of claim 1, wherein said biodegradable covering is effective to inhibit or reduce formation of scar tissue in and around said breast implant or inhibits or reduces capsular contracture in and around said implant when said breast implant is disposed in said biodegradable covering, and implanted in a patient.

13. A breast implant assembly comprising:
a biodegradable covering having elastomeric properties and a $T_g$ of less than about 40° C., said biodegradable covering include one or more drugs consisting of anti-microbial agents, and at least one of an anesthetic and anti-inflammatory agent; and
a breast implant, said breast implant and said biodegradable covering being preassembled such that said breast implant is disposed within at least a portion of said biodegradable covering, said biodegradable covering being in contact with but not adhered to said breast implant whereby said breast implant can move relative to said biodegradable covering when said breast implant is disposed within said biodegradable covering.

14. A biodegradable covering for a breast implant, said biodegradable covering comprising one or more biodegradable polymer layers comprising a sheet, film or mat of nanofibers, and including an outer surface and an inner surface for non-adherent contact with an outer surface of said breast implant, whereby said inner surface of said biodegradable covering can be in contact with but not adhered to said breast implant, said one or more biodegradable polymer layers include one or more drugs consisting of antimicrobial agents, and at least one of an anesthetic and anti-inflammatory agent.

15. The biodegradable covering of claim 14 wherein said one or more drugs is an antimicrobial agent.

16. The biodegradable covering of claim 15 wherein said antimicrobial agent is selected from the group consisting of rifampin, minocycline, gentamicin, vancomycin, triclosan, novobiocin, cephalosporin, alone or in combination.

17. The biodegradable covering of claim 14 wherein said one or more biodegradable polymer layers comprises a tyrosine-derived polyarylate.

18. The biodegradable covering of claim 14 wherein said one or more biodegradable polymers comprises a synthetic tyrosine-containing polymer.

19. The biodegradable covering of claim 14 wherein said one or more biodegradable polymer layers comprises electrospun nanofibers.

20. A biodegradable covering for a breast implant comprising a plurality of biodegradable polymer layers having elastomeric properties, said biodegradable covering having an outer surface, an inner surface for contact with an outer surface of said breast implant, and a flexible opening allowing insertion of said breast implant through said flexible opening in said biodegradable covering, said plurality of biodegradable polymer layers including a first biodegradable polymer layer comprising said inner surface and comprising a drug-impermeable biodegradable barrier layer for preventing drugs from contacting said breast implant when said breast implant is disposed within said biodegradable covering, and including at least one additional biodegradable polymer layer including one or more drugs whereby a predetermined drug release profile for said biodegradable covering can be provided wherein said one or more drugs consists of antimicrobial agents, and at least one of an anesthetic and anti-inflammatory agent.

21. The biodegradable covering of claim 20 wherein said at least one additional biodegradable polymer layer comprises a plurality of additional biodegradable polymer layers, each of said plurality of biodegradable polymer layers including one or more drugs incorporated therein.

22. The biodegradable polymer covering of claim 21 wherein said one or more drugs incorporated in each of said plurality of additional biodegradable polymer layers comprises a different drug.

23. A kit comprising a breast implant and a biodegradable covering according to claim 1, 14, or 20.

24. The biodegradable claim 1 including a plurality of said biodegradable polymer layers, wherein the layer forming said inner surface of said biodegradable covering is free of said one or more drugs and the layer forming said outer surface of said biodegradable covering comprises said one or more drugs.

25. The biodegradable claim 24, wherein the layer forming said inner surface is a drug impermeable, biodegradable barrier layer capable of preventing one or more drugs from contacting the breast implant when the breast implant is disposed within said biodegradable covering.

26. The biodegradable claim 24, wherein the layer forming said inner surface is smooth and the layer forming said outer surface is textured.

27. The biodegradable claim 1 including a plurality of said biodegradable polymer layers, wherein the layer forming said inner surface is free of said one or more drugs, the layer forming said outer surface comprises said one or more drugs and one or more polymeric layers between the layer forming said inner surface and the layer forming said outer surface comprise said one or more drugs.

28. The biodegradable claim 1, wherein the $T_g$ is in a range of about 20° C. to about 30° C.

29. The biodegradable claim 1, wherein said one or more biodegradable polymer layers comprises one to five layers.

* * * * *